(12) United States Patent
Mewissen et al.

(10) Patent No.: US 6,464,714 B1
(45) Date of Patent: Oct. 15, 2002

(54) IRRADIATION DEVICE FOR PERSONAL CARE

(75) Inventors: Jan Alfons Catharina Mewissen; Marcel Thedoor Petrus Schroor, both of Drachten (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 108 days.

(21) Appl. No.: 09/644,150

(22) Filed: Aug. 23, 2000

(30) Foreign Application Priority Data

Aug. 27, 1999 (EP) .............................. 99202771

(51) Int. Cl.⁷ ................................................ A61N 5/06
(52) U.S. Cl. .......................................... 607/90; 607/94
(58) Field of Search ...................... 607/88–95

(56) References Cited

U.S. PATENT DOCUMENTS

| | | | | |
|---|---|---|---|---|
| 4,660,561 A | * | 4/1987 | Nielsen | 607/91 |
| 4,703,184 A | * | 10/1987 | Wolff | 607/94 |
| 4,829,608 A | * | 5/1989 | Stevens et al. | 607/94 |
| 5,303,322 A | * | 4/1994 | Winston et al. | 385/129 |

* cited by examiner

Primary Examiner—Linda C. M. Dvorak
Assistant Examiner—H M. Johnson
(74) Attorney, Agent, or Firm—Ernestine C. Bartlett

(57) ABSTRACT

A light-emitting apparatus, such as a sun-tanning apparatus, has a housing enclosing a light source and other components, and a wall made of a translucent material through which light and other radiation passes to a user. The wall has a first surface facing the light source, and a second surface facing away from the source. To provide light scattering, so that a user does not see the image of the light source or non-light-emitting components, at least one of the surfaces, preferably the first surface only, has a surface structure divided into at least two areas which scatter light while still radiating a sparkling light. Each of these areas has a mutually different surface structure, preferably formed of a respective pattern of elementary structural shapes.

9 Claims, 1 Drawing Sheet

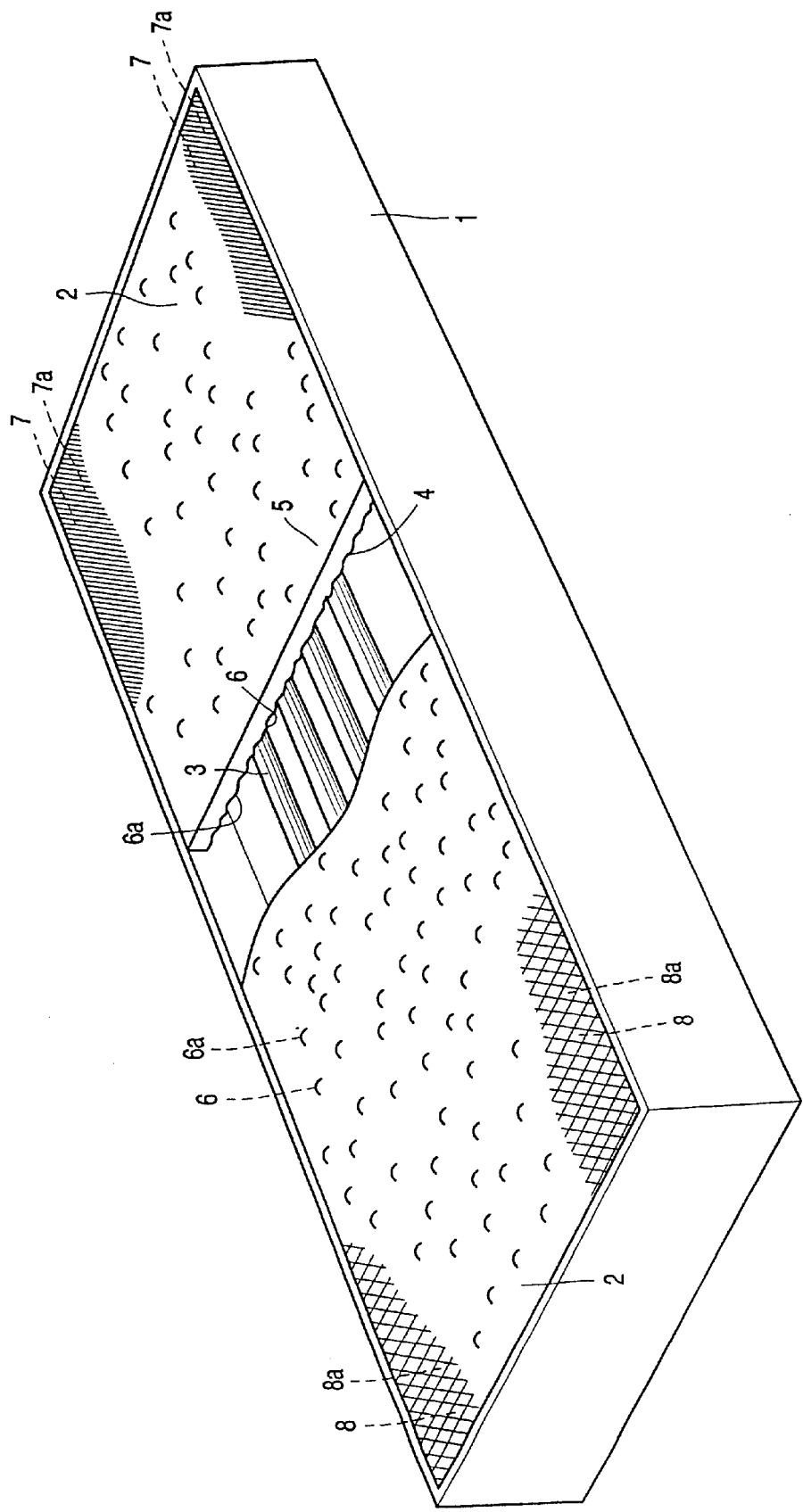

IRRADIATION DEVICE FOR PERSONAL CARE

BACKGROUND OF THE INVENTION

The invention relates to an irradiation device for personal care which comprises a housing with a light source and with a wall manufactured from a translucent material, which wall has a first surface facing the light source and a second surface facing away from the light source.

Such an irradiation device is known from DE 197 14 234 A1.

In the known device, a wall manufactured from a translucent material with a first and a second surface is formed by a frosted plate which is fastened to a housing and which covers a light source, formed by UV lamps, in the housing. The first surface faces the UV lamps, the second surface faces away from the UV lamps. The frosted plate serves to counteract that bright light originating from the light source shines into the eyes of a user or bystander near the device and serves to counteract that components inside the housing come directly into view.

It is a disadvantage of the known device that light leaving the device through the wall manufactured from the translucent material is not very sparkling. Light rays are very strongly scattered by the frosted plate, which renders the light issuing from the device comparatively dull. Although on the one hand looking at the device during operation by a user or bystanders near the device should not be rendered unpleasant by bright light shining into their eyes, on the other hand the appearance of the device during operation should contribute to a user's perception that the irradiation function is adequately performed. Light of low brightness gives rise to the idea in a user that the irradiation function is performed less well, which is disadvantageous for the quality perception which the user has in relation to the irradiation device.

SUMMARY OF THE INVENTION

It is an object of the invention to provide a device of the kind mentioned in the opening paragraph in which it is counteracted that bright light hits the eyes of a user or bystander, and it is counteracted that the components in the housing come directly into view, but where the light issuing from the device has a more sparkling appearance.

According to the invention, this object is achieved by means of a device which is characterized in that at least one of the two surfaces has at least one area with a surface structure consisting of said material. The fact that at least one of the two surfaces has at least one area with a surface structure consisting of the material was found to make the scattering of the light rays originating from the light source sufficiently great for preventing them shining brightly into the eyes of the user or bystander and for rendering the components invisible, while on the other hand the scattering is limited to such an extent that the light issuing from the device is more sparkling. This benefits a comfortable viewing of the device and is favorable for the user's quality perception of the irradiation device. Since the surface structure consists of the translucent material itself and is accordingly integral with the wall, no additional components are required for achieving a more sparkling light.

It is favorable when at least one of the two surfaces has a number of areas which have a surface structure consisting of the translucent material. At least one of the areas screens off the light source in this embodiment, while other areas screen off, for example, further components of the irradiation device, such as the supply unit and electronic devices, so that the direct view of these components in the housing is also scattered and as a result taken away from the user or bystander. This gives the irradiation device an attractive appearance in operation and out of operation, while it offers the possibility of giving the interior of the device a comparatively less fine finish, which is less expensive, because it is not observed from the outside.

It is favorable furthermore when at least two of the areas have mutually differing surface structures. The surface structures can thus be adapted to the components which they cover. The areas screening off the light source have, for example, a first surface structure, while the remaining areas screening off further components have a second surface structure or several other surface structures. The choice of the various surface structures which are to cover various areas offers the further possibility of adapting the appearance of the wall and the sparkling quality of the radiated light to, for example, the size, the light source, and further components of the envisaged embodiment of the irradiation device. Various embodiments of the device according to the invention are possible. One embodiment of the device according to the invention is characterized in that it is a suntanning device.

BRIEF DESCRIPTION OF THE DRAWING

The device according to the invention will be explained in more detail below with reference to the drawing, in which FIG. 1 shows an embodiment of the irradiation device according to the invention in perspective view.

DESCRIPTION OF THE PREFERRED EMBODIMENTS

The device shown in FIG. 1 is a suntanning device for the entire body and comprises a housing 1, a number of light sources 3 inside the housing 1, and a wall 2 manufactured from a translucent material and having a first surface 4 facing the light sources 3 and a second surface 5 facing away from the light sources 3. Part of the wall 2 has been left out in the Figure so as to show the several UV lamps which form the light sources here. The first surface 4 has a number of areas 6, 7, and 8 which have several surface structures 6a, 7a, and 8a, respectively, consisting of the translucent material. The surface structures are comparatively coarse and have a regular or irregular pattern of elementary structural shapes. In this embodiment, the wall 2 is manufactured from polymethyl methacrylate (PMMA). The area 6 with the surface structure 6a in this embodiment screens off the light sources 3, while the area 7 with the surface structure 7a and the area 8 with the surface structure 8a each cover further components, such as the supply unit and the electronic devices. The surface structures 6a, 7a, and 8a in this embodiment have respective patterns of droplets, ridges, and rasters, but they may be formed by alternative types of elementary structural shapes. This offers a considerable freedom in design, so that the appearance of the translucent wall can be adapted to the envisaged embodiment of the irradiation device. The use of the surface structure 6a renders the scattering of the light rays originating from the light source sufficiently great, so that the light hits the eyes of the user or a bystander near the device in a less concentrated form, while scattering of the light is still limited to the extent that the device emits a sparkling light. Furthermore, the surface structures 7a, 8a on the wall also blur the view of said further components on the inside of the housing, so that said components are no longer visible to the user. This is again favorable for irradiation devices in which the light source emits invisible radiation, because the irradiation device is given an attractive appearance because the direct view of the components in the housing is scattered by the surface structures and is thus taken away from the user or bystander. The second surface 5, which faces away from the light source and faces the user, is smooth in this embodiment, which is more comfortable for the user of the device who lies on this second surface 5 of the device during suntanning.

It is noted that the invention also covers irradiation devices in which the surface structures are present on the second surface 5 only, which faces away from the light source. An example of such an irradiation device is, for example, a facial tanning apparatus, where the user is not in contact with the apparatus during operation, so that an area with a surface structure on the second surface 5 facing the user is not unpleasant for the user. This gives the apparatus a more attractive appearance. In addition, surface structures may be present both on the first surface 4 and on the second surface 5. This offers the possibility of adapting the degree of sparkling of the radiated light to the envisaged embodiment of the irradiation device.

It is further noted that the wall 2 with the surface structure consisting of the material may be manufactured in that the translucent material, PMMA in this embodiment, is molded in liquid form between two glass plates. At least one of the glass plates has a surface structure at the side which comes into contact with the material in liquid form which is a negative of the surface structure of the wall 2 to be obtained after the molding and curing processes. This surface structure should be chosen such that the wall 2 can be cleanly unmolded from between the glass plates after curing. For the manufacture of the wall 2 with a number of areas which have a number of surface structures consisting of the translucent material, at least one of the glass plates may be composed from smaller glass plates with different surface structures which are fastened on a carrier. Said surface structures will then be present at the side of the glass plate which will come into contact with the material in liquid form.

What is claimed is:

1. An irradiation device for personal care which comprises a housing with a light source and with a wall manufactured from a translucent material, which wall has a first surface facing the light source and a second surface facing away from the light source, and one of the two surfaces has a surface structure consisting of said material and arranged to scatter light passing through the one surface, characterized in that said one surface has at least two areas having mutually differing surface structures, the surface structure of one of said areas being formed by elementary structural shapes, and the surface structure of the other of said areas being formed by shapes different from said elementary structural shapes.

2. A device as claimed in claim 1, further comprising other components not emitting light, characterized in that a first of said areas screens off said light source, and a second of said areas screens off at least one of said other components.

3. A device as claimed in claim 1, characterized in that the surface structure of said one of said areas is a pattern of droplets.

4. A device as claimed in claim 3, characterized in that the surface structure of said other of said areas is a pattern of ridges.

5. An irradiation device for personal care which comprises a housing with a light source and other components not emitting light and with a wall manufactured from a translucent material, which wall has a first surface facing the light source and a second surface facing away from the light source, and one of the two surfaces has a surface structure consisting of said material and arranged to scatter light passing through the one surface, characterized in that said one surface has at least two areas having mutually differing surface structure shapes, a first of said areas being arranged to screen off said light source, and a second of said areas being arranged to screen off at least one of said other components.

6. A suntanning device comprising a housing with a light source and other components not emitting light and with a wall manufactured from a translucent material, which wall has a first surface facing the light source and a second surface facing away from the light source, and one of the two surfaces has a surface structure consisting of said material and arranged to scatter light passing through the one surface, characterized in that said one surface has at least two areas having mutually differing surface structure shapes, a first of said areas being arranged to screen off said light source, and a second of said areas being arranged to screen off at least one of said other components.

7. A suntanning device as claimed in claim 6, characterized in that the mutually differing surface structure shapes are different elementary structural shapes.

8. A suntanning device as claimed in claim 7, characterized in that one of said structural shapes is a pattern of droplets.

9. A suntanning device as claimed in claim 8, characterized in that the other of said structural shapes is a pattern of ridges.

* * * * *